United States Patent [19]

Waterhouse et al.

[11] Patent Number: 5,714,667
[45] Date of Patent: Feb. 3, 1998

[54] MICE LACKING EXPRESSION OF CTLA-4 RECEPTOR

[75] Inventors: Paul David Waterhouse, London; Tak Wah Mak, Toronto, both of Canada

[73] Assignee: Amgen Canada Inc., Mississauga, Canada

[21] Appl. No.: 554,133

[22] Filed: Nov. 6, 1995

[51] Int. Cl.$^6$ .............................. C12N 5/00; C12N 15/00
[52] U.S. Cl. .......................... 800/2; 435/172.3; 435/69.1; 435/91.2; 435/325; 435/69.3; 435/320.1; 536/23.1; 536/23.5; 536/23.53; 536/24.31; 935/23; 935/78; 935/79; 935/81; 935/70; 935/71
[58] Field of Search .............................. 800/2; 435/172.3, 435/69.1, 240.2, 91.2, 69.3, 320.1, 325; 536/23.1, 23.5, 23.53, 24.31; 935/23, 78, 79, 81, 70, 71

[56] References Cited

PUBLICATIONS

Capecchi, Scientific American, vol. 270, pp. 34–41, Mar. 1994.
Shahinian et al., Science, vol. 261, p. 609, 1993.
Brunet et al., Nature, vol. 328, p. 267, 1987.
Tivol, et al., Immunity, 3, 541–547, Nov., 1995.
Allison et al., Science, 270:932–933 [1995].
Gribben et al., Proc. Nat. Acad. Sci. USA, 92:811–815 [1995].
Harper et al., J. of Immunology, 147(3):1037–1044 [1991].
Krummel et al., J. Cellular Biochem., Suppl. 0, 18D:429 [1994].
Lane et al., J. Exp. Med., 179:819–830 [1994].
Ronchese et al., J. Exp. Med., 179:809–817 [1994].
Waterhouse et al., Science, 270, 985–988 [1995].
Immen, Wallace, The Globe and Mail, Nov. 10, 1995.
Papp, Leslie, Toronto Star,[1995].
Krummel et al., J. Exp. Med., 182: 459 [1995].

*Primary Examiner*—Jasemine C. Chambers, PHD.
*Assistant Examiner*—Jill D. Schmuck
*Attorney, Agent, or Firm*—Nancy A. Oleski; Ron Levy; Steven M. Odre

[57] ABSTRACT

Disclosed is a mouse in which expression of the gene encoding the CTLA-4 receptor is suppressed. Also disclosed is a nucleic acid construct useful in preparing such a mouse, and a cell line containing such construct.

6 Claims, 5 Drawing Sheets

MICE LACKING EXPRESSION OF CTLA-4 RECEPTOR

BACKGROUND

1. Field of the Invention

This invention relates to a mouse in which production of the protein encoded by the endogenous gene CTLA-4 receptor has been completely suppressed.

2. Description of Related Art

Cytolytic (cytotoxic) T-lymphocyte-associated antigen number 4 receptor ("CTLA-4 receptor"; also referred to herein as "CTLA-4") is a protein that is expressed on the surface of a class of immune system cells known as T-cells. The cDNA encoding mouse CTLA-4 receptor has been cloned and sequenced (Brunet et al., *Nature*, 328:267 [1987]). In mice, CTLA-4 cDNA has approximately 76 percent homology with another T-cell surface receptor protein called CD28, and the two genes are located in close proximity to each other on mouse chromosome 1 (Harper et al., *J. Immunol*, 147:1037 [1991]; Howard et al., *Immunogenet.*, 33:74 [1991]). Both CTLA-4 receptor and CD28 bind to the protein ligands B7-1 and B7-2 (Linsley et al., *Immunity*, 1:793 [1994]; Linsley et al., *J. Exp. Med.*, 173: 721 [1991]); B7-1 and B7-2 are expressed on the surface of immune system cells known as antigen presenting cells ("APCs"). Due to its similarity to CD28, the CTLA-4 receptor has been postulated to play a role in T-cell activation.

Various studies have been conducted in an attempt to identify the precise role of CTLA-4 receptor in immune system function.

Gribben et al. (*Proc. Natl. Acad. Sci. USA*, 92:811–815 [1995]) describe studies wherein cross-linking of the CTLA-4 receptor on previously activated T-cells can purportedly mediate apoptosis (cell death) of these cells.

Krummel et al. (*J. Exp. Med.*, 182:459[1995]) describe the use of anti CTLA-4 receptor monoclonal antibodies and CTLA-4 receptor-Ig fusion proteins that have been used to assess the expression pattern of CTLA-4 receptor.

Ronchese et al. (*J. Exp. Med.*, 179:809–817 [1994]) describe a mouse containing a transgene encoding a soluble form of CTLA-4 receptor. The mouse is purportedly defective in T-cell dependent antibody production.

Lane et al. (*J. Exp. Med.*, 179:819–830 [1994]) describe a transgenic mouse purportedly expressing a soluble form of CTLA-4 receptor.

In view of the importance of T-cell function in the immune system, there is a need in the art to provide in vivo systems for screening drugs useful in modulating T-cell activity, particularly as such activity relates to the CTLA-4 receptor.

Accordingly, it is an object of this invention to provide a mammal in which one or more genes involved in T-cell regulation, such as the CTLA-4 receptor, have been suppressed.

This and other such objects will readily be apparent to one of ordinary skill in the art.

SUMMARY OF THE INVENTION

In one embodiment, the present invention provides a rodent comprising the gene encoding a CTLA-4 receptor, wherein one allele of the gene has been disrupted. Optionally, the rodent may be a mouse.

In another embodiment, this invention provides a rodent comprising the gene encoding a CTLA-4 receptor, wherein both alleles of the gene have been disrupted. Optionally, the rodent may be a mouse.

In yet another embodiment, this invention provides a rodent comprising a disrupted CTLA-4 receptor mutation, wherein the disruption results in a null mutation of the gene encoding a CTLA-4 receptor. Optionally, the rodent may be a mouse.

In still another embodiment, this invention provides a nucleic acid molecule comprising a CTLA-4 receptor knockout construct. Optionally, this construct may be inserted into an amplification and/or an expression vector, and the vector may be useful for transforming a prokaryotic or eukaryotic cell, or an embryo.

In one additional embodiment, the present invention provides a murine E14 embryonic stem cell line comprising a CTLA-4 receptor knockout construct.

DETAILED DESCRIPTION OF THE INVENTION

Figures 1A, 1B:
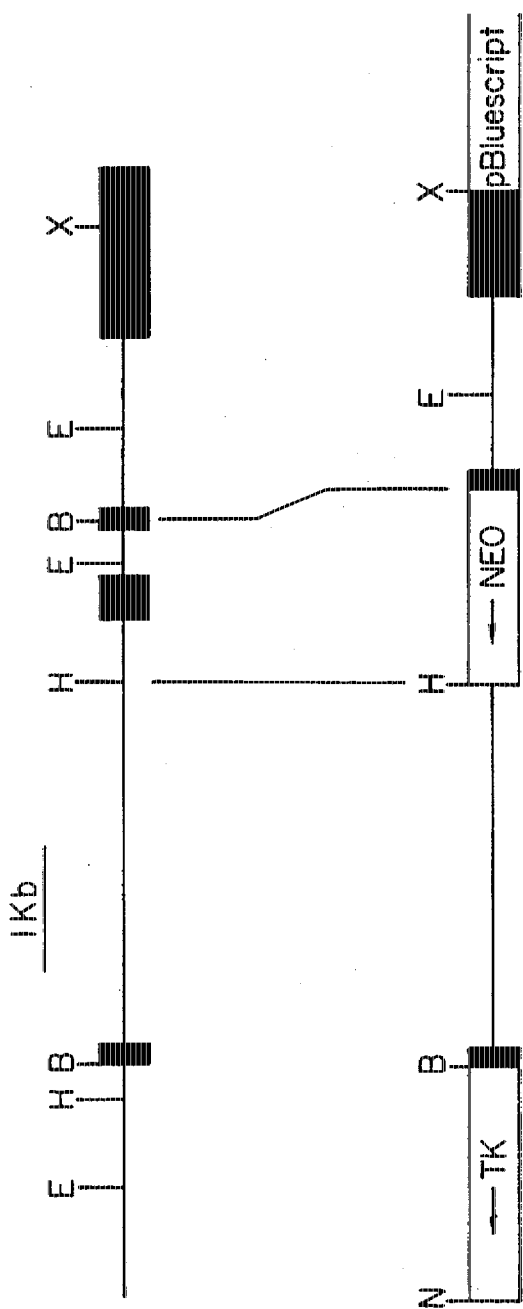
FIG. 1 depicts preparation of a CTLA-4 receptor knockout construct. Restriction sites are indicated as follows: "E" is EcoRI; "H" is HindIII; "B" is BamHI; "X" is XhoI; "N" is NotI. Exons are indicated as black boxes, and introns as thin black lines. (A) depicts a fragment of the CTLA-4 receptor native gene containing exons 1–4 and introns 1–3. (B) depicts the knockout construct in which the thymidine kinase (TK) cassette and the neomycin (neo) cassette have been ligated into the CTLA-4 receptor gene.

The term "knockout" refers to partial or complete reduction of the expression of at least a portion of a polypeptide encoded by an endogenous gene (such as CTLA-4 receptor) of a single cell, selected cells, or all of the cells of a mammal. The mammal may be a "heterozygous knockout", wherein one allele of the endogenous gene has been disrupted. Alternatively, the mammal may be a "homozygous knockout" wherein both alleles of the endogenous gene have been disrupted.

The term "knockout construct" refers to a nucleotide sequence that is designed to decrease or suppress expression of a polypeptide encoded by an endogenous gene in one or more cells of a mammal. The nucleotide sequence used as the knockout construct is typically comprised of (1) DNA from some portion of the endogenous gene (one or more exon sequences, intron sequences, and/or promoter sequences) to be suppressed and (2) a marker sequence used to detect the presence of the knockout construct in the cell. The knockout construct is inserted into a cell containing the endogenous gene to be knocked out. The knockout construct can then integrate with one or both alleles of the endogenous CTLA-4 gene, and such integration of the CTLA-4 knockout construct can prevent or interrupt transcription of the full-length endogenous CTLA-4 gene. Integration of the CTLA-4 knockout construct into the cellular chromosomal DNA is typically accomplished via homologous recombination (i.e., regions of the CTLA-4 knockout construct that are homologous or complimentary to endogenous CTLA-4 DNA sequences can hybridize to each other when the knockout construct is inserted into the cell; these regions can then recombine so that the knockout construct is incorporated into the corresponding position of the endogenous DNA).

Typically, the knockout construct is inserted into an undifferentiated cell termed an embryonic stem cell (ES cell). ES cells are usually derived from an embryo or blastocyst of the same species as the developing embryo into which it can be introduced, as discussed below The phrases "disruption of the gene", "gene disruption", "suppressing expression", and "gene suppression", refer to insertion of a CTLA-4 receptor nucleotide sequence knockout construct into a homologous region of the coding region of the endogenous CTLA-4 receptor gene (usually containing one or more exons) and/or the promoter region of this gene so as to decrease or prevent expression of the full length CTLA-4 receptor in the cell. Insertion is usually accomplished by homologous recombination. By way of example, a nucleotide sequence knockout construct can be prepared by inserting a nucleotide sequence comprising an antibiotic resistance gene into a portion of an isolated nucleotide sequence encoding CTLA-4 receptor that is to be disrupted. When this knockout construct is then inserted into an embryonic stem cell ("ES cell"), the construct can integrate into the genomic DNA of at least one CTLA-4 receptor allele. Thus, many progeny of the cell will no longer express CTLA-4 receptor at least in some cells, or will express it at a decreased level and/or in a truncated form, as at least part of the endogenous coding region of CTLA-4 receptor is now disrupted by the antibiotic resistance gene.

The term "marker sequence" refers to a nucleotide sequence that is (1) used as part of a larger nucleotide sequence construct (i.e., the "knockout construct") to disrupt the expression of CTLA-4, and (2) used as a means to identify those cells that have incorporated the CTLA-4 knockout construct into the chromosomal DNA. The marker sequence may be any sequence that serves these purposes, although typically it will be a sequence encoding a protein that confers a detectable trait on the cell, such as an antibiotic resistance gene or an assayable enzyme not naturally found in the cell. The marker sequence will also typically contain either a homologous or heterologous promoter that regulates its expression.

The terms "rodent" and "rodents" refer to all members of the phylogenetic order Rodentia including any and all progeny of all future generations derived therefrom.

The term "murine" refers to any and all members of the family Muridae, including without limitation, rats and mice.

The term "progeny" refers to any and all future generations derived or descending from a particular mammal, i.e., a mammal containing one or more knockout constructs inserted into its genomic DNA, whether the mammal is heterozygous or homozygous for the knockout construct. Progeny of any successive generation are included herein such that the progeny, the F1, F2, F3, generations and so on indefinitely containing the knockout construct are included in this definition.

The term "immunomodulatory" refers to changes in the level of expression or activity (i.e., a detectable increase or decrease) of any component (i.e., cell, polypeptide, protein, and/or nucleic acid molecule) of the immune system in a mammal as compared to the average expression or activity of that same component for the same mammalian species that has not been genetically altered (i.e., the wild-type). Immunomodulation may be detected by assaying the level of B cells, any type of T cells, antigen presenting cells, and/or any other cells believed to be involved in immune function. Additionally or alternatively, immunomodulation may be detected by evaluating 1) the level of expression of particular genes believed to have a role in the immune system, 2) the level of particular compounds such as cytokines (interleukins and the like), immunoglobulins, and/or other molecules that have a role in the immune system such as, for example, receptors for various cytokines, and/or 3) the level of particular enzymes, proteins, and the like that are involved in immune system functioning.

Included within the scope of this invention is a mammal in which one or both CTLA-4 receptor alleles, as well as one or both alleles of another gene(s), have been knocked out. Such a mammal can be generated by repeating the procedures set forth herein for generating a CTLA-4 receptor knockout mammal but using another gene, or by breeding two mammals, one with one or both alleles of CTLA-4 knocked out, and one with one or both alleles of a second gene knocked out, to each other, and screening for those offspring that have the double knockout genotype (whether a double heterozygous or a double homozygous knockout genotype, or a variation thereof).

Also included within the scope of this invention is a mammal in which 1) one or both CTLA-4 receptor alleles, and optionally one or both alleles of another gene(s), have been knocked out, and 2) one or more transgenes (i.e., exogenous DNA sequence(s) encoding a polypeptide(s) that may or may not be naturally occurring in the mammal) have been inserted.

Knockout Technology

1. Isolation of the CTLA-4 Gene

A CTLA-4 receptor knockout construct is typically prepared by isolating a portion of the genomic or cDNA CTLA-4 receptor nucleotide sequence (usually encoding at least one exon and one intron), and inserting a marker sequence into the CTLA-4 receptor sequence. The CTLA-4 receptor gene or gene fragment to be used in preparing this construct may be obtained in a variety of ways. Generally, the CTLA-4 receptor DNA molecule will be at least about 1 kilobase (kb) in length, and preferably will be 3–4 kb in length, thereby providing sufficient complementary sequence for recognition with chromosomal DNA (i.e., homologous recombination) when the knockout construct is introduced into the genomic DNA of the ES cell (discussed below).

A naturally occurring genomic CTLA-4 receptor fragment or cDNA molecule to be used in preparing the knockout construct can be obtained using methods well known in the art such as those described by Sambrook et al. (*Molecular Cloning: A Laboratory Manual*, Cold Spring Harbor Laboratory Press, Cold Spring Harbor, N.Y. [1989]). Such methods include, for example, PCR amplification of a particular DNA sequence using oligonucleotide primers, or screening a genomic library prepared from cells or tissues that contain the CTLA-4 receptor gene with a cDNA probe encoding at least a portion of the same or a highly homologous CTLA-4 receptor gene in order to obtain at least a portion of the CTLA-4 receptor genomic sequence. Alternatively, if a cDNA sequence is to be used in a knockout construct, the cDNA may be obtained by screening a cDNA library (preferably one prepared from tissues or cells such as T cells that express CTLA-4 receptor, where the tissues or cells are derived from the same or a similar species of mammal as that to be rendered the knockout mammal) with oligonucleotide probes, homologous cDNA probes, or antibodies (where the library is cloned into an expression vector). If a promoter sequence is to be used in the knockout construct, synthetic DNA probes or primers can be designed for screening a genomic library or for amplification using PCR, respectively.

Where the DNA sequence of the endogenous CTLA-4 receptor gene is known, a DNA fragment encoding the desired portion of such gene may be manufactured synthetically, using chemical synthesis methods such as those described by Engels et al., (*Angew. Chem. Int. Ed. Engl.*, 28:716–734 [1989]). These methods include inter alia, the phosphotriester, phosphoramidite, and H-phosphonate methods of nucleic acid synthesis. Typically, the genomic DNA fragment to be prepared will be several hundred base pairs in length. Since the chemical synthesis methods set forth herein can be used to make nucleic acid sequences of up to about 100 base pairs, the native genomic DNA can be synthesized in 100 bp fragments which can then be ligated together using standard DNA ligation methods.

The CTLA-4 receptor genomic DNA fragment or CTLA-4 receptor cDNA molecule prepared for use in the knockout construct must be generated in sufficient quantity for genetic manipulation. Amplification may be conducted by 1) placing the fragment into a suitable vector and transforming bacterial or other cells that can rapidly amplify the vector, 2) by PCR amplification, 3) by synthesis with a DNA synthesizer, or 4) by other suitable methods.

2. Preparation of a CTLA-4 Receptor Knockout Construct

The CTLA-4 receptor genomic DNA fragment, cDNA molecule, or PCR fragment to be used in making the CTLA-4 receptor knockout construct can be digested with one or more restriction enzymes selected to cut at a location (s) such that a second DNA molecule encoding a marker gene can be inserted in the proper position within the CTLA-4 receptor genomic DNA fragment, cDNA molecule, or PCR fragment to be used in the construct. The proper position for marker gene insertion is one that will serve to decrease or prevent transcription and/or expression of full length endogenous CTLA-4 receptor gene. This position will depend on various factors such as the available restriction sites in the sequence to be cut, whether an exon sequence or a promoter sequence, or both is (are) to be interrupted, and whether several isoforms of CTLA-4 receptor exist in the mammmal (due to alternative splicing) and only one such isoform is to be disrupted. Preferably, the enzyme(s) selected for cutting the CTLA-4 genomic DNA, cDNA molecule, or PCR fragment will generate a longer arm and a shorter arm, where the shorter arm is at least about 300 base pairs (bp). In some cases, it will be desirable to actually delete a portion or even all of one or more introns or exons of this native genomic or cDNA molecule. In these cases, the CTLA-4 receptor genomic DNA, cDNA molecule, or PCR fragment can be cut with appropriate restriction endonucleases such that a fragment of the proper size and proper location can be removed.

The marker gene used in the knockout construct can be any nucleic acid molecule that is detectable and/or assayable after it has been incorporated into the genomic DNA of the ES cell, and ultimately the knockout mammal, however typically it is an antibiotic resistance gene or other gene whose expression or presence in the genome can easily be detected. Preferably, the marker gene encodes a polypeptide that does not naturally occur in the mammal. The marker gene is usually operably linked to its own promoter or to another strong promoter such as the thymidine kinase (TK) promoter or the phosphoglycerol kinase (PGK) promoter from any source that will be active or can easily be activated in the cell into which it is inserted; however, the marker gene need not have its own promoter attached, as it may be transcribed using the promoter of the gene to be knocked out. In addition, the marker gene will normally have a polyA sequence attached to its 3' end; this sequence serves to terminate transcription of the marker gene. Preferred marker genes are any antibiotic resistance gene such as neo (the neomycin resistance gene) and beta-gal (beta-galactosidase).

After the CTLA-4 receptor genomic DNA fragment, cDNA molecule, or PCR fragment has been digested with the appropriate restriction enzyme(s), the marker gene molecule can be ligated with the native genomic DNA or cDNA molecule using methods well known to the skilled artisan and described in Sambrook et al., supra. In some cases, it will be preferable to insert the marker sequence in the reverse or antisense orientation with respect to the CTLA-4 receptor nucleic acid sequence; this reverse insertion is preferred where the marker gene is operably linked to a particularly strong promoter.

The ends of the DNA molecules to be ligated must be compatible; this can be achieved by either cutting all fragments with those enzymes that generate compatible ends, or by blunting the ends prior to ligation. Blunting can be done using methods well known in the art, such as for example by the use of Klenow fragment (DNA polymerase I) to fill in sticky ends. After ligation, the ligated constructs can be screened by selective restriction endonuclease digestion to determine which constructs contain the marker sequence in the desired orientation.

The ligated DNA knockout construct may be transfected directly into embryonic stem cells (discussed below), or it may first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

3. Transfection of Embryonic Stem Cells

The CTLA-4 receptor knockout construct is typically transfected into stem cells derived from an embryo (embryonic stem cells, or "ES cells") ES cells are undifferentiated cells that are capable of taking up extrachromosomal DNA and incorporating it into their chromosomal DNA. Generally, the ES cells used to produce the knockout mammal will be of the same species as the knockout mammal to be generated. Thus for example, mouse embryonic stem cells will usually be used for generation of knockout mice.

The embryonic stem cell line used is typically selected for its ability to integrate into and become part of the germ line of a developing embryo so as to create germ line transmission of the knockout construct. Thus, any ES cell line that is believed to have this capability is suitable for use herein. Preferred ES cell lines for generating knockout mice are murine cell lines D3 and E14 (American Type Culture Collection, 12301 Parklawn Drive, Rockville, Md. 20852-1776 USA, catalog nos. CRL 1934 and CRL 1821, respectively). The cells are cultured and prepared for DNA insertion using methods well known to the skilled artisan such as those set forth by Robertson (in: *Teratocarcinomas and Embryonic Stem Cells: A Practical Approach*, E. J. Robertson, ed. IRL Press, Washington, DC. [1987]), by Bradley et al. (*Current Topics in Devel. Biol.*, 20:357–371 [1986]) and by Hogan et al. (*Manipulating the Mouse Embryo: A Laboratory Manual*, Cold Spring Harbor Laboratory Press, Cold Spring Harbor, N.Y. [1986]).

Insertion (also termed "transfection") of the knockout construct into the ES cells can be accomplished using a variety of methods well known in the art including for example, electroporation, microinjection, and calcium phosphate treatment (see Lovell-Badge, in Robertson, ed., supra). A preferred method of insertion is electroporation.

The CTLA-4 receptor knockout construct DNA molecules to be transfected into the cells can first be linearized if the knockout construct has previously been inserted into a circular vector. Linearization can be accomplished by digesting the DNA with a suitable restriction endonuclease selected to cut only within the vector sequence and not within the knockout construct sequence. The isolated CTLA-4 receptor knockout construct DNA can be added to the ES cells under appropriate conditions for the insertion method chosen. Where more than one construct is to be introduced into the ES cells, the DNA molecules encoding each construct can be introduced simultaneously or sequentially. Optionally, homozygous CTLA-4 receptor knockout ES cells may be generated by adding excessive CTLA-4 receptor knockout construct DNA to the cells, or by conducting successive rounds of transfection in an attempt to achieve homologous recombination of the knockout construct on both endogenous CTLA-4 receptor alleles.

If the ES cells are to be electroporated, the ES cells and knockout construct DNA are exposed to an electric pulse using an electroporation machine and following the manufacturer's guidelines for use. After electroporation, the cells are typically allowed to recover under suitable incubation conditions. The cells are then screened for the presence of the knockout construct.

Screening the ES cells can be accomplished using a variety of methods, but typically, one screens for the presence of the marker sequence portion of the knockout construct. Where the marker gene is an antibiotic resistance gene, the cells can be cultured in the presence of an otherwise lethal concentration of antibiotic. Those cells that survive have presumably integrated the knockout construct. If the marker gene is other than an antibiotic resistance gene, a Southern blot of the ES cell genomic DNA can be probed with a sequence of DNA designed to hybridize only to the marker sequence. If the marker gene is a gene that encodes an enzyme whose activity can be detected (e.g., beta-galactosidase), the enzyme substrate can be added to the cells under suitable conditions, and the enzymatic activity of the marker gene can be analyzed.

The knockout construct may integrate into several locations in the ES cell genome, and may integrate into a different location in each cell's genome, due to the occurrence of random insertion events; the desired location of insertion is within the CTLA-4 receptor endogenous gene sequence. Typically, less than about 1-5 percent of the ES cells that take up the knockout construct will actually integrate the knockout construct in the desired location. To identify those cells with proper integration of the knockout construct, chromosomal DNA can be extracted from the cells using standard methods such as those described by Sambrook et al., supra. This DNA can then be probed on a Southern blot with a probe or probes designed to hybridize to the knockout construct DNA digested with (a) particular restriction enzyme(s). Alternatively, or additionally, a specific genomic DNA sequence can be amplified by PCR with probes specifically designed to amplify that DNA sequence such that only those cells containing the knockout construct in the proper position will generate DNA fragments of the proper size.

4. ES Cell Incorporation/Implantation of Embryos

After suitable ES cells containing the knockout construct in the proper location have been identified, the cells can be incorporated into an embryo. Incorporation may be accomplished in a variety of ways.

A preferred method of incorporation of ES cells is by microinjection into an embryo that is at the blastocyst stage of development. For microinjection, about 10-30 cells are collected into a micropipet and injected into a blastocyst to integrate the ES cell into the developing blastocyst.

The suitable stage of development for the blastocyst is species dependent, however for mice it is about 3.5 days. The blastocysts can be obtained by perfusing the uterus of pregnant females. Suitable methods for accomplishing this are known to the skilled artisan, and are set forth for example by Bradley (in Robertson, ed., supra).

While any blastocyst of the right age/stage of development is suitable for use, preferred blastocysts are male and have genes coding for a coat color or other phenotypic marker that is different from the coat color or other phenotypic marker encoded by the ES cell genes. In this way, the offspring can be screened easily for the presence of the knockout construct by looking for mosaic coat color or other phenotypic marker (indicating that the ES cell was incorporated into the developing embryo). Thus, for example, if the ES cell line carries the genes for white fur, the embryo selected will preferably carry genes for black or brown fur.

An alternate method of preparing an embryo containing ES cells that possess the knockout construct is to generate "aggregation chimeras". A morula of the proper developmental stage (about 2½ days old for mice) is isolated. The *zona pellucida* can be removed by treating the morula with a solution of mild acid for about 30 seconds, thereby exposing the "clump" of cells that comprise the morula. Certain types of ES cells such as the R1 cell line for mice can then be co-cultured with the moruta cells, forming an aggregation chimera embryo of morula and ES cells.

A refinement of the aggregation chimera embryo method can be used to generate an embryo comprised of essentially only those ES cells containing the knockout construct. In this technique, a very early stage zygote (e.g., a two-cell stage zygote for mice) is given a mild electric shock. This shock serves to fuse the nuclei of the cells in the zygote thereby generating a single nucleus that has two-fold (or more) the DNA of a naturally occurring zygote of the same developmental stage. These zygotic cells are excluded from the developing embryo proper, and contribute only to forming accessory embryonic structures such as the extraembryonic membrane. Therefore, when ES cells are co-cultured with the zygotic cells, the developing embryo is comprised exclusively of ES cells.

After the ES cells have been incorporated, the aggregation chimera or transfected embryo can be implanted into the uterus of a pseudopregnant foster mother. While any foster mother may be used, preferred foster mothers are typically selected for their ability to breed and reproduce well, and for their ability to care for their young. Such foster mothers are typically prepared by mating with vasectomized males of the same species. The pseudopregnant stage of the foster mother is important for successful implantation, and it is species dependent. For mice, this stage is about 2–3 days pseudopregnant.

5. Screening for the CTLA-4 Receptor Knockout Gene

Offspring that are born to the foster mother may be screened initially for mosaic coat color or other phenotype marker where the phenotype selection strategy (such as coat color, as described above) has been employed. In addition, or as an alternative, chromosomal DNA obtained from tail tissue of the offspring may be screened for the presence of the knockout construct using Southern blots and/or PCR as described above. The offspring that are positive for the CTLA-4 receptor knockout construct will typically be heterozygous, although some homozygous knockouts may exist, and can typically be detected by visually quantifying the amount of probe that hybridizes to the Southern blots.

If homozygous knockout mammals are desired, they can be prepared by crossing those heterozygous offspring believed to carry the knockout construct in their germ line to each other; such crosses may generate homozygous knockout animals. If it is unclear whether the offspring will have germ line transmission, they can be crossed with a parental or other strain and the offspring screened for heterozygosity. Homozygotes may be identified by Southern blotting of equivalent amounts of genomic DNA from mammals that are the product of this cross, as well as mammals of the same species that are known heterozygotes, and wild-type mammals. Probes to screen the Southern blots for the presence of the knockout construct in the genomic DNA can be designed as set forth above.

Other means of identifying and characterizing the knockout offspring are also available. For example, Northern blots can be used to probe mRNA obtained from various tissues of the offspring for the presence or absence of transcripts encoding either the gene knocked out, the marker gene, or both. In addition, Western blots can be used to assess the level of expression of the gene knocked out in various tissues of these offspring by probing the Western blot with an antibody against the protein encoded by the gene knocked out, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Both the heterozygous and homozygous CTLA-4 receptor knockout mammals of this invention will have a variety of uses, since CTLA-4 receptor has been implicated in modulating the level of T cell proliferation. One such use will be to use the mammal as an in vivo screening system for drugs that affect T cell levels and/or T-cell activation (proliferation). It is known that T cell levels increase in certain autoimmune diseases, as well as in certain inflammatory diseases (e.g., arthritis). In addition, certain diseases such as AIDS generally result in decreased T cell counts which results in immunosuppression. As such, the claimed mammals may be used to screen for drugs useful for altering T cell levels and/or T cell activation/proliferation, i.e., drugs that either enhance or inhibit these activities, depending on the disease under study.

Screening for such useful drugs typically involves administering the candidate drug over a range of doses to the mammal, and assaying at various time points for the immunomodulatory effect(s) of the drug on the immune disorder being evaluated. Such assays would include, for example, looking for increased or decreased T cell levels, increased or decreased immunoglobulin production, increased or decreased levels and/or activity of chemical messengers such as interleukins, and/or increased or decreased levels of expression of a particular gene(s) involved in the immune response.

For example, patients undergoing chemotherapy often experience immunosuppression. It would be desirable to activate the immune system of such individuals by administering to the patient a therapeutic agent capable of producing such an effect. A mammal of the present invention could be used to screen a variety of compounds, either alone or in combination, to determine whether partial or total restoration or activation of the immune response results from the use of such drug.

The same strategy could be applied to find compounds that would be useful in suppressing the inflammatory response observed in many patients with arthritis, or compounds that would be useful in suppressing the autoimmune phenomenon observed in patients with rheumatoid arthritis and lupus.

In addition, a mammal of the present invention can be useful for evaluating the development and function of various components of the immune system, and for studying the effects of particular gene mutations. For example, in a mammal not expressing CTLA-4, one can analyze the effect of the lack of such expression on other components of the immune system.

Yet another use for the claimed mammals is in studying tumor proliferation; the claimed mammals may have an increased ability to fight cancer due to the lack of negative regulation of T cell activation (i.e., the T cells in these mammals are constantly activated).

Other uses of the claimed mammals and compounds will be readily apparent to one of skill in the art.

The invention will be more fully understood by reference to the following examples. These examples are not to be construed in any way as limiting the scope of this invention.

EXAMPLES

Example 1

Preparation of a CTLA-4 Knockout Construct

Splenocytes were obtained from C57BL/6 mice by removing the spleens and passing them through a fine mesh. The splenocytes were incubated in Iscove's modified Dulbecco's medium (about ten percent fetal calf serum and 50 µM beta-mercaptoethanol) with approximately 2.5 µg/ml of concanavalin A ("ConA") for approximately 36 hours at about 37° C. After incubation, total RNA was prepared from these cells using the method of Chomczynski et al. (*Anal. Biochem.*, 162:156–159 [1987]). cDNA was then prepared from the RNA using reverse transcriptase. To identify the cDNA encoding CTLA-4 receptor, the polymerase chain reaction (PCR) method was used. The PCR primers were:

```
TGGAACTCGTCGACCCACCGCCAT-
    ACTTTGTGGGCATGGGCAAC            (SEQ ID NO: 1)

TCACCATCCGCCGGCGCAACTGAGCCCT-
    GTGACAGCCTCATCTAG               (SEQ ID NO:2)
```

Thirty cycles of PCR were conducted using the following parameters: 94° C. for 30 seconds, 70° C. for 30 seconds, and 72° C. for 60 seconds.

The PCR products were run on an approximately one percent agarose gel, and a band of the predicted size of about 1.038 kilobase (kb) was cut out of the gel and ligated into the cloning vector pCRII using the TA cloning kit (Invitrogen Company, San Diego, Calif.) for sequencing. This approximately 1 kb fragment was found to contain the entire coding region for the CTLA-4 receptor gene, but was not a full length cDNA as it lacked the 3' non-coding region.

To obtain the murine CTLA-4 receptor genomic clone, total DNA was isolated from the mouse embryonic stem cell line E-14 (originally isolated as described by Handyside et al., *Roux. Arch. Devel. Biol.*, 198:48 [1989]) using standard procedures for genomic DNA isolation as set forth in Sambrook et al., supra. The DNA was digested with the restriction endonuclease BamHI, and then ligated into the vector Lambda ZAP Express (Stratagene, La Jolla, Calif.) to generate an E-14 genomic DNA library. The 1 kb CTLA-4 receptor cDNA clone was used to screen this library, and six clones were obtained when the library was screened at a stringency of about 65° C. in about 40 mM sodium phosphate, pH 7.4. These clones were confirmed to contain a portion of the CTLA-4 receptor genomic sequence using the following exon II/exon III specific primers:

```
TGGAACTCGTCGACCCACCGCCAT-
    ACTTTGTGGGCATGGGCAAC            (SEQ ID NO:3)

AGAATCCGGGCATGGTTCTGGATC            (SEQ ID NO: 4)
```

In addition, the following exon IV specific primers were also used:

```
AGGCCGTTTATGAAGAAGAAGGAG            (SEQ ID NO: 5)

CTTTGGAACCACTGGCTATGTCAC            (SEQ ID NO: 6)
```

Recovery of the cloned sequences and plasmid amplification was conducted following the manufacturer's protocol for the Lambda Zap Express kit. One clone (fragment 1) was then prepared as a BamHI/HindIII fragment and was approximately 3 kb. A second clone was prepared as a BamHI/XhoI fragment (fragment 2) and was about 2.3 kb in length. Fragment 1 contained exon 1 and most of intron 1 (see FIG. 1) and fragment 2 contained the 3' half of exon 3, all of intron 3, and most of exon 4 (see FIG. 1). These fragments, along with a neo cassette containing a PGK (phosphoglycerate kinase) promoter derived from the pKJ-1 vector (Tybutewicz et al., *Cell*, 65:1153–1163 [1991]; Adra et al., *Gene*, 60:65–74 [1987]) and a TK cassette (thymidine kinase gene with a PGK promoter; Tybutewicz et al., supra) were directionally cloned, using standard ligation techniques, into the vector pBluescript (Stratagene, La Jolla, Calif.) to generate a knockout construct containing, from 5' to 3', the TK cassette, CTLA-4 receptor fragment 1, the neo cassette, and CTLA-4 receptor fragment 2 (see FIG. 1). Both the TK cassette and the neo cassette were ligated in the antisense direction. To confirm proper ligation, the cloning junctions were sequenced.

This vector, containing all components in the proper orientation, was linearized with NotI and then electroporated into E-14 embryonic stem cells as follows: about 5 pmol of linearized DNA was added to about $5 \times 10^6$ ES cells in a volume of about 800 μl of culture media. The cells were pulsed at about 0.34 kilovolts and about 250 μF, and each vial of cells was then plated on to two 10 cm cell culture plates. The plates were precoated with 1 percent gelatin, and contained about 10 ml of DMEM medium (Gibco/BRL, Grand Island, N.Y.), 15 percent fetal calf serum (Gibco/BRL, Grand Island, N.Y. or equivalent from Hyclone Labs, Logan, Utah), and leukemia inhibitory factor (Fung-Leung et al. *Cell*, 65:443–449 [1991]), $10^{-5}$ M B-mercaptoethanol, 2 mM L-glutamine, and 1 mM sodium pyruvate. After two days in culture, the cells were screened for those containing the neo and TK cassettes by culturing the cells in the presence of gangcyclovir and G418 (Cappecchi, *Science*, 244:1288 [1989]; Shahinian et al., *Science*, 261:609 [1993]); surviving cells were collected, and those that had undergone homologous recombination were then selected for by culturing in medium containing G418 but not gangcyclovir. To confirm homologous recombination, the cells that grew in the presence of G418 were then screened by mini-Southern blot (Ramirez-Solis et al., *Anal. Biochem.*, 201:331–335 [1992]) using genomic DNA prepared from the cells and cut with EcoRI.

Samples of E14 cells that have undergone homologous recombination to incorporate the CTLA-4 receptor knockout construct in their genomic DNA have been deposited with the American Type Culture Collection ("ATCC", 12301 Parklawn Drive, Rockville, Md. 20852, USA) as accession number CRL 11953, with a deposit date of 28 June 1995.

Figure 5A:
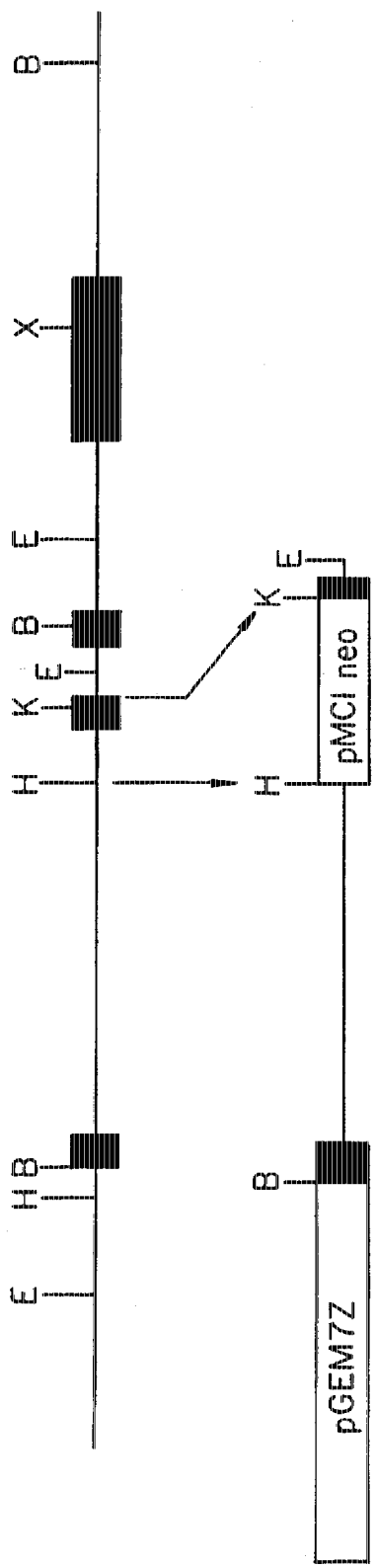
FIG. 5 (A and B) depicts two other CTLA-4 receptor knockout constructs that were generated. The restriction site abbreviations are the same as described in FIG. 1. "K" is KpnI.
Figure 5B:
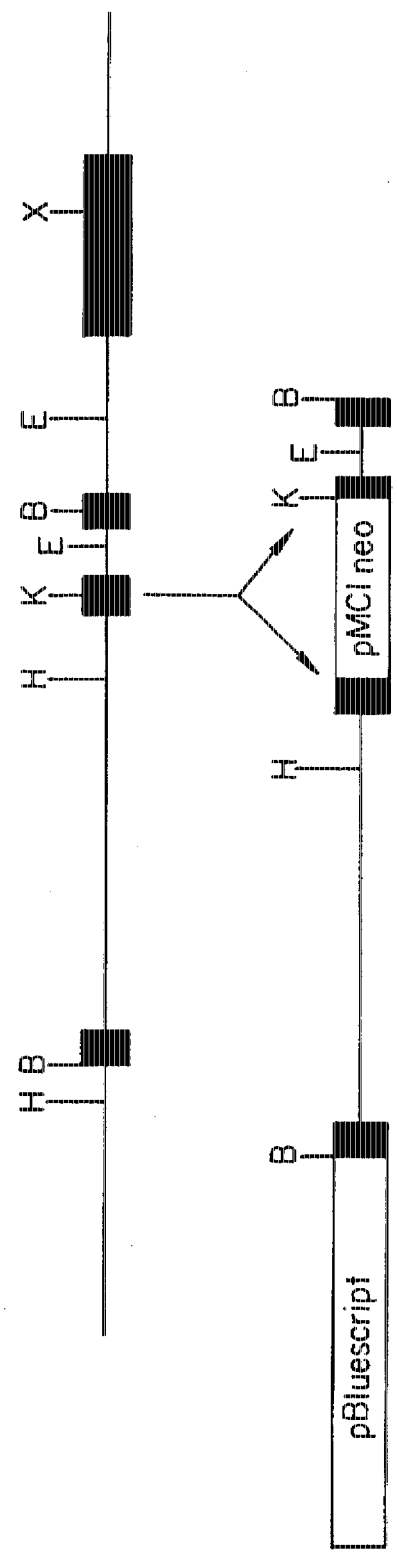

In addition to the CTLA-4 receptor knockout construct described above, two other constructs were generated and are depicted in FIG. 5A and 5B. All attempts to generate ES cells that had undergone homologous recombination were unsuccessful using these two constructs.

The first construct was prepared from a CTLA-4 receptor genomic fragment from a Balb/c mouse genomic library. This fragment, which contained exons 1–4 and introns 1–3, was digested first with BamHI and EcoRI to obtain a fragment containing exons 1 and 2, intron 1, and the 5' half of intron 2. The fragment was then digested with KpnI which cuts near the 3' end of exon 2. The pMC1neo cassette was then inserted into this KpnI site. This construct is shown in FIG. 5A.

The second construct was generated from the CTLA-4 receptor fragment as shown in FIG. 1A. This fragment was digested with BamHI to generate a smaller fragment containing exons 1–3 and introns 1 and 2. The pMC1neo cassette was then inserted into exon 2 by digesting the CTLA-4 receptor fragment with KpnI. This construct is shown in FIG. 5B.

Example 2

Preparation of CTLA-4 Receptor Knockout Mice

The E14 cells containing the CTLA-4 receptor knockout construct were inserted into fertilized embryos (blastocysts) that were approximately 3.5 days old, which were obtained from C57BL/6 mice by perfusing the uterus of female C57BL/6 mice that had been mated with male mice. Insertion was accomplished by microinjecting about 15–30 cells into each blastocyst. The embryos were then implanted into CD1 pseudo pregnant female mice at day 2.5 post coitum for gestation. The chimeric male offspring of these foster mothers were screened for agouti coat color and were crossed with female C57BL/6 females. Germline transmission of the knockout construct was determined by coat color of the $F_1$ pups; agouti pups were identified as heterozygous CTLA-4 receptor knockouts. These $F_1$ pups were crossed with each other to generate $F_2$ homozygotes. The homozygotes were identified by PCR amplification using one set of primers directed to exon 2, and a second set of primers directed to the neo cassette. In addition, Southern blot analysis of genomic DNA cut with EcoRI and probed with a SpeI/SspI CTLA-4 receptor specific probe was used to confirm homologous recombination.

Example 3

Characterization of CTLA-4 Receptor Knockout Mice

The following procedures were used for all analyses described below in which qualitative and/or quantitative determination of various cell surface proteins was accomplished by immunofluorescence. Single cell suspensions of thymus (to generate thymocytes), lymph nodes, spleen and bone marrow were prepared according to procedures set forth by Penninger et al. (*Science*, 260:358 [1993]). Typically, about $1 \times 10^6$ cells per well (using a 96 well flat bottom microtiter place) were incubated for about 30 minutes at about 4° C. in about 100 µl of immunofluorescence buffer (PBS, 1 percent bovine serum albumin, and 0.01 percent sodium azide) in the presence of the appropriate immunofluorescence labeled antibody. The cells were then washed in the same immunofluorescence buffer, and were analyzed on a FACScan using a Lysis II program (Becton Dickinson, Mountain View, Calif.). The antibodies used are set forth below, and the concentration of each antibody used is as indicated in about 100 µl of immunofluorescence buffer: fluorescein diisothiocyanate ("FITC") labeled anti-CD69 at about 0.5 µg/100 µl; phycoerythrin ("PE") labeled anti-CD44 at about 0.5 µg/100 µl; PE-labeled anti CD28 at about 1 µg/100 µl; FITC or PE labeled anti-CD4 at about 0.1 µg/100 µl; FITC-labeled (or biotin labeled, see below) anti CD-8 at about 0.1 µg/100 µl; FITC or PE-labeled anti-pan αβ TCR at about 1 µg/100 µl; PE-labeled anti-CTLA-4 at about 0.5 µg/100 µl; PE-labeled anti-B7.1 at about 1 µg/100 µl; PE-labeled anti-B7.2 at about 1 µg/100 µl; FITC-labeled anti-Thy1.2 at about 1 µg/100 µl; FITC (or biotin; see below) labeled anti-CD5 at about 0.5 µg/100 µl; PE-labeled anti-Fas at about 0.6 µg/100 µl; PE-labeled anti CD43 at about 1 µg/100 µl; and FITC or PE-labeled anti B220 at about 0.5 µg/100 µl. Biotinylated antibodies were incubated under the same conditions as the fluorescent antibodies, however they were visualized by addition of Streptavidin-RED 670 (Gibco BRL, Gaithersburg, Md.). All antibodies were purchased from Pharmingen (San Diego, Calif.).

To characterize CTLA-4 receptor protein expression, T cells from 21 day old wild type heterozygous knockout and homozygous knockout mice were obtained by surgical removal of lymph nodes, followed by disruption of the lymph nodes on a fine mesh screen and passing the single cell suspension over a mouse T cell enrichment column to remove non-T cells. The T cells were then cultured in Iscove's modified Dulbecco's medium (containing about ten percent fetal calf serum plus 50 µM beta-mercaptoethanol) in 10 cm plates coated with anti-hamster IgG antiserum (Jackson Laboratories, West Grove, Pa.) followed by hamster anti-mouse CD3 antibody (Pharmingen, San Diego, Calif.). After 24 hours, ConA cell supernatant (obtained from culturing rat splenocytes for about 48 hours in the presence of about 2.5 µg/ml ConA and then passing the cells through a fine mesh filter) was added at about 10 percent (v/v). This supernatant provides a source of IL-2 and other cytokines. The culture medium for the T cells was replaced after 3 days. On day 4, the T cells were recovered by centrifugation and labeled with both mouse FITC labeled -anti-TCRαβ and mouse PE labeled-anti-CTLA-4, or with biotinylated mouse monoclonal antibodies directed to either CD25, CD44 or CD69. The labeling was conducted using the methods described above. T cells from all three mouse strains showed high levels of expression of CD25, CD44 and CD69. T cells from homozygous knockout mice did not express the CTLA-4 receptor, although this protein was expressed at a high level on T cells derived from wild-type and heterozygous knockout mice.

Anatomical evaluation of four week old CTLA-4 receptor wild type, heterozygous knockout and homozygous knockout mice indicated that the lymph nodes and spleen were slightly enlarged in the heterozygous knockout mice as compared with the wild type, and greatly enlarged in the homozygous knockout mice. The data are shown in Table I.

TABLE I

| Genotype | Wet weight (mg) | | Lymphocyte number (×10⁷) | |
| --- | --- | --- | --- | --- |
| | Lymph nodes | Spleen | Lymph nodes | Spleen |
| CTLA-4$^{+/+}$ | 71 | 69 | 1.3 | 3.1 |
| CTLA-4$^{+/-}$ | 97 | 77 | 1.7 | 3.1 |
| CTLA-4$^{-/-}$ | 540 | 145 | 28.0 | 7.7 |
| CTLA-4$^{-/-}$ | 380 | 501 | 12.0 | 16.5 |

The organs were isolated from 4 week old littermates.

The number of cells was determined using a hemocytometer. As can be seen, the number of lymphocytes in both lymph nodes and spleen was greater in the homozygous knockout mice as compared to the other two strains.

In addition to having enlarged spleens and lymph nodes, the thymus of the homozygous knockout mice was consistently smaller as compared to the other two strains.

Histology of various tissues of a 28 day old CTLA-4 receptor knockout mouse revealed extensive accumulation of activated lymphocytes within lymph nodes, thymus, and splenic white pulp, which obscured the cortico-medullary compartmentalization of the thymus and zonal distribution of T and B cell dependent areas in spleen and lymph nodes.

The CTLA-4 receptor heterozygous mice were healthy with normal growth and reproductive traits. Homozygous CTLA-4 receptor knockout mice were healthy at birth, but died or became moribund at about 3-4 weeks of age. In addition, diffuse and focal lymphocyte infiltration was prominent in heart, lung, bone marrow, liver and pancreas, but not in kidneys of the CTLA-4 receptor homozygous knockout mice. Myocardial infarctions as detected by histology were prominent with granulation tissue formation.

The phenotypes of thymocytes and peripheral T cells were analyzed for wild type, heterozygous knockout and homozygous knockout mice. For thymocytes, CD4 and CD8 cell populations were measured by FACscan analysis. Both CD4 and CD8 single-positive populations were increased about 4-fold, and the proportion of CD4/CD8 double positive T cells was reduced in CTLA-4 receptor homozygous knockout mice.

T cell selection markers such as CD5, CD69 and CD44, all of which can undergo changes in the level of expression in response to positive and negative thymic selection (Bendelac et al., *J. Exp. Med.*, 175:731 [1992]) were expressed at comparable levels on thymocytes from all three mouse strains. Expression of these markers was assessed using the appropriate immunofluorescence labeled antibodies and methods as set forth above.

T cells were isolated from enlarged lymph nodes of homozygous CTLA-4 receptor knockout mice using methods for T cell isolation described above. These cells showed up-regulation of CD69, CD44 and CD25 expression, as measured by immunofluorescence as described above, and down-regulation of Mel-14 expression (Mel-14 expression was measured using a PE-labeled anti Mel-14 antibody purchased from Pharmingen, San Diego, Calif.). Up-regulation of CD69, CD44 and CD25 expression was also observed in spleen from the CLTLA-4 receptor homozygous knockout mice, although no significant differences over wild type were observed for the CD4/CD8 ratio. TCRαβ profiles, as measured by immunofluorescence as described above, from spleen and bone marrow of CTLA-4 receptor homozygous knockout mice showed expansion of activated T cells in these organs.

The B cell population in lymph node and spleen tissues was assessed for both wild type and homozygous knockout mice as follows. Lymph node B cells of homozygous knockout mice and wild type mice were isolated using methods described above and double immunolabeled with either anti-B220 (PE) and anti-Fas (biotin), anti-B220 (biotin) and anti-CD43 (PE), or anti-B220 (FITC) and anti-CD5 (biotin), using the immunostaining procedures set forth above. The B cells from homozygous knockouts displayed an up regulation of the B7-2 antigen expression, but not of B7-1 antigen expression, as measured by immunofluorescence as described above. In addition, expression of the Fas antigen, CD43 and CD5 were all up-regulated on B cells of the homozygous knockout mice.

Figure 2:
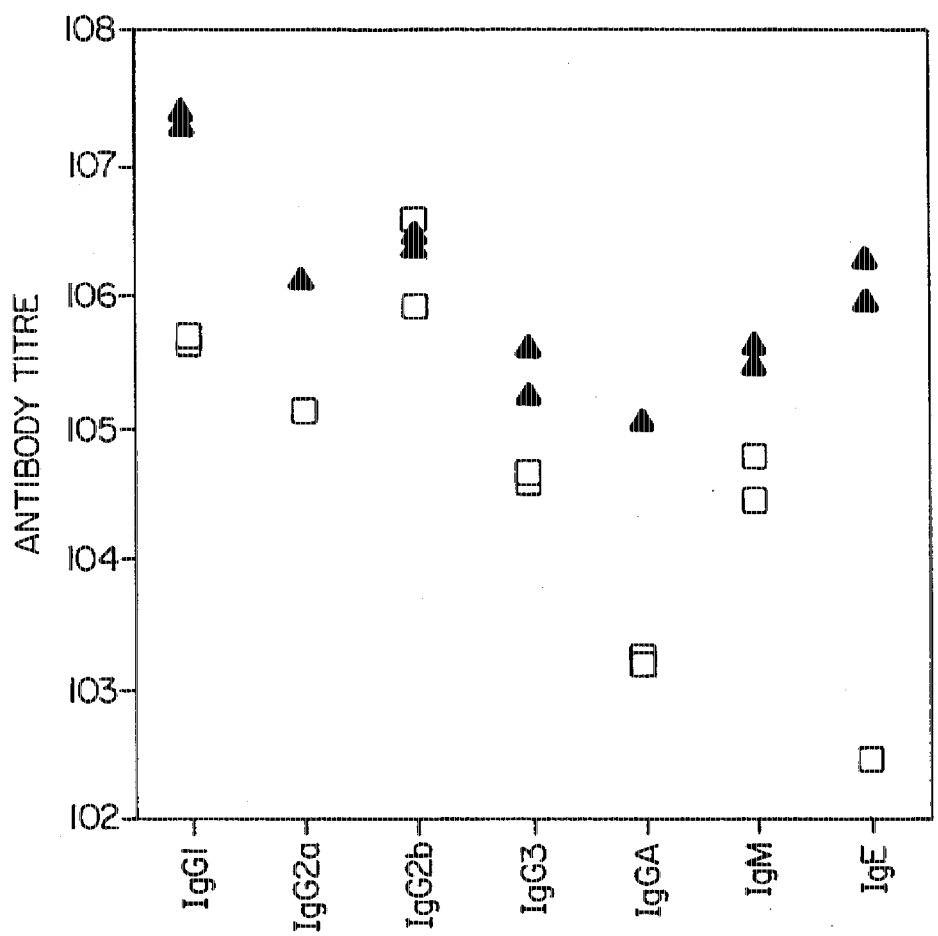
FIG. 2 depicts the antibody titer (indicated exponentially) of various Ig classes and subclasses in wild type (open squares) and homozygous knockout (dark triangles) CTLA-4 receptor knockout mice.

The basal Ig serum levels for the homozygous knockout mice and wild type mice were measured using a mouse Ig subtype ELISA kit (Genzyme, Cambridge, Mass.). As shown in FIG. 2, the homozygous knockout mice had consistently higher Ig levels, ranging from about a 10-fold increase as compared to wild type for IgG2a, IgG2b, IgG3 and IgM, to about a 100-fold increase for IgG1 and IgA, to about several thousand fold for IgE.

Figure 3:
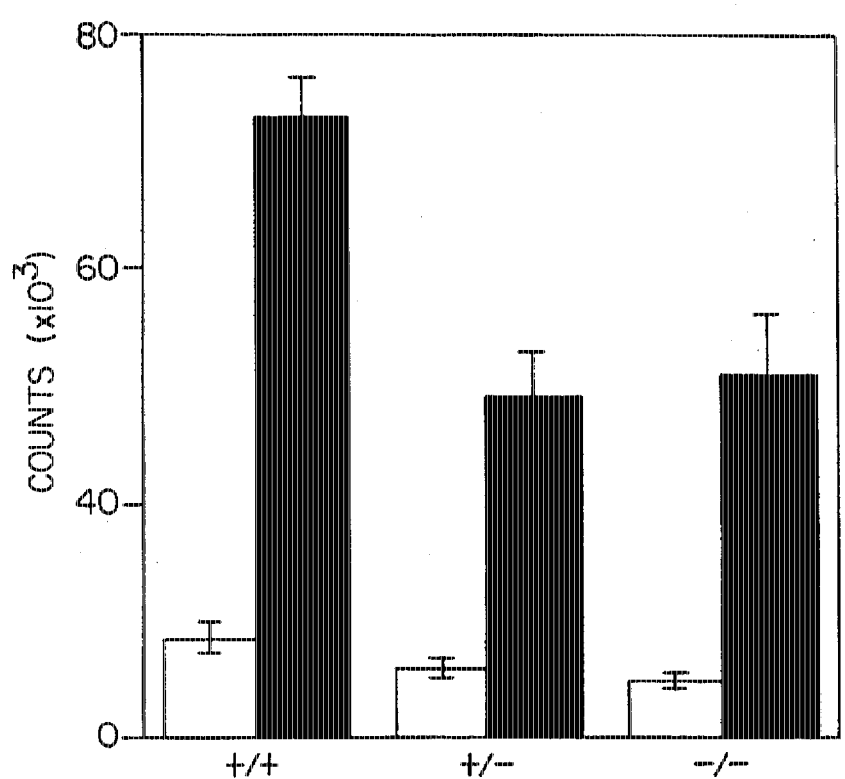
FIG. 3 depicts the proliferative ability of T-cells derived from lymph nodes. Open bars show the response to autologous stimulator cells ($H2^{b/b}$) and solid bars show allo-responses to splenic stimulators from Balb/c mice ($H2^{d/d}$). The X axis indicates CTLA-4 wild type (+/+), heterozygous CTLA-4 receptor knockout (+/−) and homozygous CTLA-4 receptor knockout (−/−) cells. Triplicate samples were measured and are presented as mean thymidine uptake +/− standard deviation.

To assess the proliferative ability of T cells derived from lymph nodes, $^3$H-thymidine analyses were conducted for wild type, heterozygous knockout and homozygous knockout mice. Responder T cells were purified from lymph nodes of 22 day old mice using mouse T-cell enrichment columns (R&D Systems, Minneapolis, Minn.). Irradiated (2000 rads) and T cell depleted splenic antigen presenting cells (T cells lysed by exposure to anti-Thy 1.2 antibody and rabbit complement incubated 1 hour at 37° C.) were co-cultured with the responder T cells (both at a density of about $5 \times 10^5$/well) for 4 days in 96 well plates and then pulsed with about 1 µCi of $^3$H- thymidine for about 16 hours. The results are shown in FIG. 3. As can be seen, the response of all three strains was comparable when the standard deviation is taken into account.

Figure 4A:
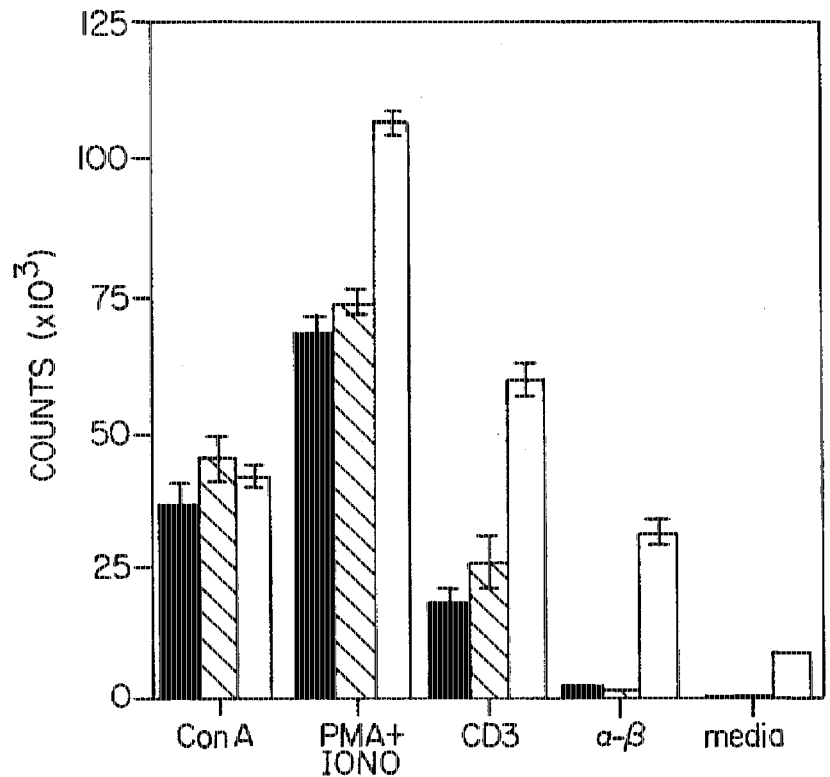
FIG. 4A–B depicts T-lymphocyte activity in culture. (A) The response of lymphocytes from wild type (dark boxes), CTLA-4 receptor heterozygous (hatched boxes) and homozygous (open boxes) knockout mice to various potential stimulators. "ConA" is concanavalin A; "PMA+IONO" is phorbol myristic acid plus calcium ionophore; "CD3" is anti-CD3 antibody; "α-β" is anti-TCRαβ antibody; "media" is media only without added stimulator. (B) The proliferation of T-lymphocytes from wild-type (+/+), heterozygous CTLA-4 receptor knockout (+/−), and homozygous knockout (−/−) mice. The y-axis is counts $\times 10^3$.
Figure 4B:
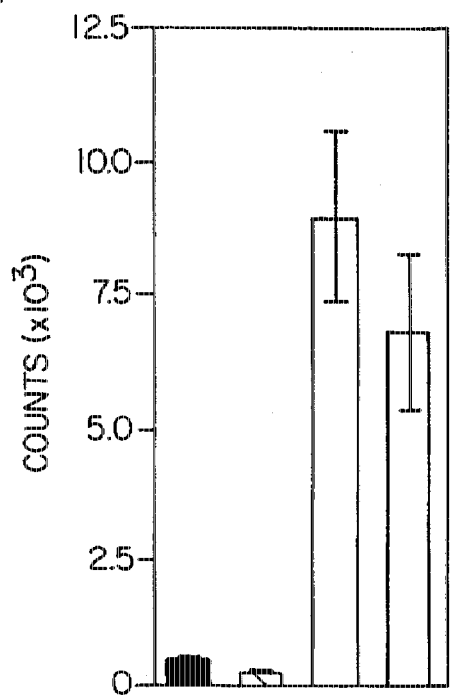

Lymphocytes from wild type, CTLA-4 receptor heterozygous knockout, and CTLA-4 receptor homozygous knockout mice were evaluated for their proliferative abilities in response to various potential stimulators. Lymphocytes isolated from lymph node tissue of littermates of the three strains were cultured for about 48 hours in flat bottom 96 well microtiter plates in medium alone (Iscove's modified Dulbecco's medium containing 10 percent fetal calf serum plus 50 µM beta-mercaptoethanol) or containing anti-TCRαβ (at about 1 µg/1 ml) anti-CD3 (at about 1 µg/1 ml), Con A (at about 2.5 µg/ml) or PMA (phorbol myristic acid at about 12 ng/ml) or calcium ionophore A23617 (at about 50 ng/ml). The cells were then pulsed with about 1 µCi of $^3$H-thymidine for about 8 hours, recovered by batch filtration onto glass fiber filters (Packard, Meriden, Conn.) and then counted on a Matrix 96 counter (Packard, Meriden, Conn.). The results are shown in FIG. 4A. As can be seen, lymphocytes from all strains responded comparably to ConA, but the homozygous knockout mice showed higher proliferation rates as compared to the wild type in response to anti-CD3 and anti-TCRαβ antibodies. T-lymphocytes from homozygous CTLA-4 receptor knockout mice displayed spontaneous proliferation for the first 24 hours when cultured in medium alone as compared to wild type and heterozygous CTLA-4 receptor knockout mice (FIG. 4B), but cells from younger (10 day old) mice with less evidence of immunopathology had little proliferation ex vivo over control (wild type) T lymphocytes.

The Fas receptor protein is constitutively expressed on the surface of T cells and is typically up-regulated when the T cells are activated. When the Fas receptor binds its ligand, which is expressed on the surface of T cells, the T cells can undergo apoptosis. To evaluate whether activated T cells lacking CTLA-4 receptor expression are susceptible to Fas receptor induced apoptosis, freshly isolated lymph node T cells were analyzed for Fas crosslinking as follows. About $2 \times 10^6$ T cells/ml from CTLA-4 receptor homozygous knockout mice and wild type mice were cultured in Iscove's medium (containing 10 percent fetal calf serum and 50 µM beta-mercaptoethanol) in the presence or absence of anti-CD3 antibody (at about 1 µg/ml) plus IL-2 (at about 20 U/ml) and with or without anti-Fas antibody (about 1 µg/ml) for about 24 hours. The number of viable cells was then determined by Trypan blue staining. The results indicated that no change in viability was apparent for wild type T cells, since they were not activated. However, the homozygous knockout T cells (which are activated, as discussed above) showed an approximately 30 percent decrease in viable cell number after 24 hours. Other researchers have found an approximately 30 percent decrease in viability of normal (wild-type), activated T cells under experimental conditions similar to those set forth above.

We claim:

1. A transgenic mouse homozygous for a disrupted CTLA-4 receptor gene, wherein said CTLA-4 receptor gene is disrupted by a selectable marker sequence introduced into said mouse or an ancestor of said mouse at an embryonic stage, and wherein said disrupted CTLA-4 receptor gene results in said mouse exhibiting enlarged lymph nodes as compared to a wild type mouse.

2. A mouse of claim 1, wherein the disruption results in a null mutation of the gene encoding a CTLA-4 receptor.

3. A CTLA-4 receptor DNA knockout construct comprising a selectable marker sequence flanked by DNA sequences homologous to the CTLA-4 receptor gene, wherein when said construct is introduced into a mouse or an ancestor of a mouse at an embryonic stage, said selectable marker sequence disrupts the CTLA-4 receptor gene in said mouse and results in said mouse exhibiting enlarged lymph nodes as compared to a wild type mouse.

4. A vector comprising the CTLA-4 receptor DNA knockout construct of claim 3.

5. A CTLA-4 receptor DNA knockout construct according to claim 3, wherein said construct consists of, 5' to 3', a thymidine kinase cassette; the CTLA-4 receptor fragment 1 containing exon 1 and most of intron 1 as depicted in FIG. 1; a neo cassette; and the CTLA-4 receptor fragment 2 containing the 3' half of exon 3, all of intron 3, and most of exon 4 as depicted in FIG. 1.

6. A mouse E14 embryonic stem cell line comprising the CTLA-4 DNA receptor knockout construct of claim 3.

* * * * *

UNITED STATES PATENT AND TRADEMARK OFFICE
CERTIFICATE OF CORRECTION

PATENT NO. : 5,714,667
DATED : February 3, 1998
INVENTOR(S) : Waterhouse et al.

It is certified that error appears in the above-identified patent and that said Letters Patent is hereby corrected as shown below:

column 3, line 29, after "below" insert --.--;

column 8, line 55, replace "moruta" with -- morula--; and column 15, line 1, replace "CLTLA-4" with -- CTLA-4--.

Signed and Sealed this

Twenty-fifth Day of August, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: other nucleic acid ( x i ) SEQUENCE DESCRIPTION: SEQ ID NO:1:

TGGAACTCGT CGACCCACCG CCATACTTTG TGGGCATGGG CAAC      44

-continued ( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

TCACCATCCG CCGGCGCAAC TGAGCCCTGT GACAGCCTCA TCTAG    45

( 2 ) INFORMATION FOR SEQ ID NO:3:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

TGGAACTCGT CGACCCACCG CCATACTTTG TGGGCATGGG CAAC    44

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

AGAATCCGGG CATGGTTCTG GATC    24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

AGGCCGTTTA TGAAGAAGAA GGAG    24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

CTTTGGAACC ACTGGCTATG TCAC    24